United States Patent [19]
Lord

[11] Patent Number: 4,758,968
[45] Date of Patent: Jul. 19, 1988

[54] METHOD AND APPARATUS FOR CONTINUOUSLY MEASURING THE VARIABILITY OF TEXTILE STRANDS

[75] Inventor: Peter R. Lord, Raleigh, N.C.

[73] Assignee: North Carolina State University, Raleigh, N.C.

[21] Appl. No.: 734,775

[22] Filed: May 16, 1985

[51] Int. Cl.[4] .................. G06F 15/46; G01L 05/04
[52] U.S. Cl. ..................... 364/552; 73/160; 364/470
[58] Field of Search .......... 73/160; 364/550–552, 364/507, 470

[56] References Cited

U.S. PATENT DOCUMENTS

| | | | |
|---|---|---|---|
| 2,465,818 | 3/1949 | Richardson | 73/160 |
| 2,679,639 | 5/1954 | Locher | 340/213 |
| 2,871,447 | 1/1959 | Hall | 324/114 |
| 3,106,762 | 10/1963 | Riera | 73/160 |
| 3,145,297 | 8/1964 | Felix | 235/183 |
| 3,287,977 | 11/1966 | Marshall et al. | 73/160 |
| 3,435,673 | 4/1969 | Felix | 73/160 |
| 3,722,260 | 3/1973 | Staheli | 73/160 |
| 3,731,069 | 5/1973 | Goto et al. | 73/160 |
| 3,752,170 | 8/1973 | Murbach | 73/160 X |
| 3,763,361 | 10/1973 | Smart | 235/183 |
| 3,808,411 | 4/1974 | Hoffmann | 235/184 |
| 3,822,590 | 7/1974 | Tharpe et al. | 73/160 |
| 3,984,895 | 10/1976 | Grice, Jr. | 73/160 |
| 4,007,457 | 2/1977 | Aeppli | 73/160 |
| 4,027,232 | 5/1977 | Domig et al. | 73/160 |
| 4,030,082 | 6/1977 | Goto | 73/160 |
| 4,045,659 | 8/1977 | Akagawa et al. | 73/160 |
| 4,051,722 | 10/1977 | Feller | 73/160 |
| 4,058,962 | 11/1977 | Spescha et al. | 73/160 |
| 4,122,703 | 10/1978 | Davis | 73/160 |
| 4,144,578 | 3/1979 | Mueller et al. | 364/551 |
| 4,152,931 | 5/1979 | Mannhart | 73/160 |
| 4,168,604 | 9/1979 | Mannhart | 73/160 |
| 4,184,361 | 1/1980 | Erken | 73/160 |
| 4,295,360 | 10/1981 | Fountain | 73/160 |
| 4,302,968 | 12/1981 | Moser | 73/160 |
| 4,306,450 | 12/1981 | Moser | 73/160 |
| 4,318,299 | 3/1982 | Morf | 73/160 |
| 4,568,875 | 2/1986 | Piso et al. | 73/160 |
| 4,584,875 | 4/1986 | Wod et al. | 73/160 |
| 4,648,054 | 3/1987 | Farah et al. | 364/552 |

Primary Examiner—Parshotam S. Lall
Assistant Examiner—Edward R. Cosimano
Attorney, Agent, or Firm—Bell, Seltzer, Park & Gibson

[57] ABSTRACT

A method and apparatus for continuously measuring the variability of an advancing textile strand is disclosed, and wherein the output signal is useful in diagnosing the source of the variations. The method includes the steps of continuously monitoring at least one selected parameter and applying the resulting signal to each of a plurality of integrating networks each having a different predetermined time constant. The output signal from each of the integrating networks is then applied to a root mean square network to produce an output which closely approximates the standard deviation of the output signal of the associated integrating network. In a further embodiment, the signal from the monitoring device is applied to an integrating network, and the output of the integrating network is applied serially to two root mean square networks. Several embodiments of a transducer are also disclosed which are designed to permit the monitoring of a number of parameters in the moving textile strand.

24 Claims, 3 Drawing Sheets

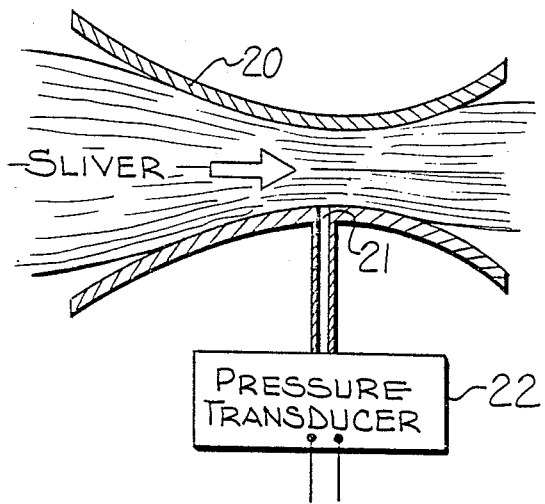
_Fig-5_
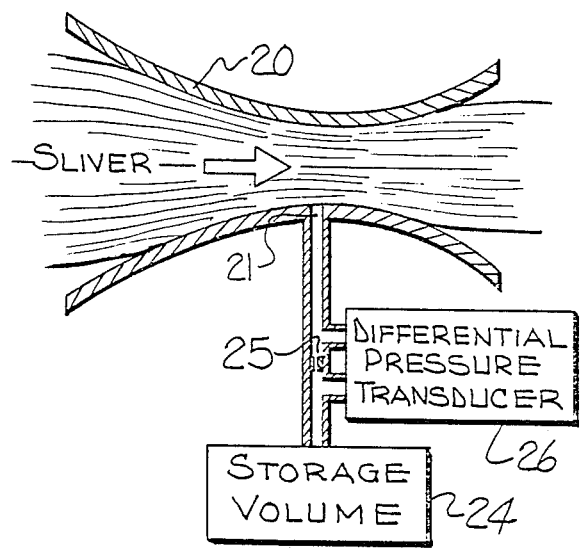
_Fig-6_
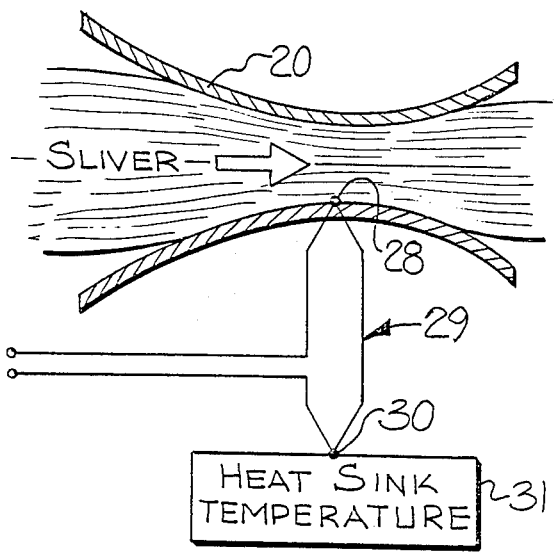
_Fig-7_
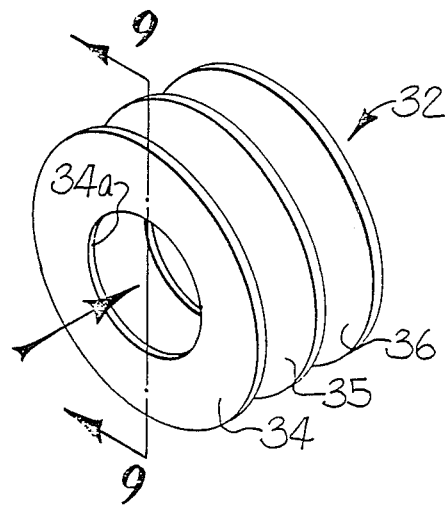
_Fig-8_

METHOD AND APPARATUS FOR CONTINUOUSLY MEASURING THE VARIABILITY OF TEXTILE STRANDS

The present invention relates to a method and apparatus for continuously measuring the variability of one or more quality related parameters of textile strands which have been subjected to a number of processing operations, and wherein the output data is useful in diagnosing the source of the variations.

As the speed of yarn processing machines, such as knitting or weaving machines, increases, there is a need for a higher quality yarn to withstand the forces imparted thereto and to produce an acceptable fabric. The yarn producing machines also require improved yarn quality as their operating speed increases. Thus there are requirements from several directions to produce better quality yarn, in terms of both strength and uniformity.

It has heretofore been recognized that the linear density of the yarn strand being processed varies along its length, and that this variation may be utilized to monitor the quality of an advancing strand. For example, it has been recognized that fibers of different compositions in a blend tend to migrate longitudinally along the strand during processing, and this migration results in variations in linear density. The variations thus impart a history of the process on the strand, which is carried from one machine to the next. Thus for example, if there has been a periodic migration in the draw frame, then that migration means that the population of the fibers presented to the next machine will vary in a more or less periodic fashion, and upon leaving the next machine, an elongated version of the original history plus a superimposed history from the next machine is carried forward. Thus the errors produced in carding, drawing, or ring spinning will all appear in the finished yarn.

Traditionally, the variability of textile strands has been measured and computed by sampling the strand after it has passed through a processing operation, which involves physically removing discrete samples to the laboratory and measuring the desired properties or attributes. The results were then used to compute the average values, standard deviations, and/or coefficients of variation, using known statistical procedures. However, this random sampling technique has the disadvantage of having relatively long delays during which large quantities of out of tolerance material may be produced. Also, it is difficult to assure that representative samples are taken, and errors may occur by reason of non-representative samples.

Yarn strand monitoring systems have been proposed which utilize electrical systems by which a variable parameter of an advancing strand is monitored. For example, these prior systems produce an output signal which is proportional to the variations of the parameter, and which is applied to a circuit in which the mean deviation in the variable parameter of the strand may be determined from the average value, or the coefficient of variation of the variable parameter may be determined, note for example U.S. Pat. Nos. 2,679,639 and 3,808,411. However, these prior monitoring systems produce outputs of only limited value in evaluating the quality of a yarn product which has been subjected to a number of different processing steps, and in diagnosing the cause of any revealed errors.

It has also been proposed that the linear density of an advancing yarn strand may be measured continuously by means of capacitive, optical, pneumatic, or other similar systems, and each of these devices has been designed to produce an electrical output signal which is proportional to the linear density. However, in many applications it is desirable to be able to efficiently monitor other parameters of the advancing strand, such as fiber finish, packing density, geometry, stiffness, and frictional characteristics, and presently known transducers are incapable of providing output signals which are representative of these additional parameters and separating the variables.

It is accordingly an object of the present invention to provide a method and apparatus for continuously measuring the variability of one or more parameters of textile strands which have been subjected to a number of separate processing steps, and which produces output data which may be used for effectively monitoring the quality of the strands as well as diagnosing the probable cause of variations in the quality.

It is also an object of the present invention to provide a transducer adapted for continuously monitoring each of a number of parameters of an advancing textile strand.

These and other objects and advantages of the present invention are achieved in the embodiments illustrated herein by the provision of a method and apparatus which includes the steps of continuously monitoring at least one selected parameter of the advancing strand and producing a continuous initial signal which is functionally related to such parameter, applying the initial signal to each of a plurality of signal integrating networks each having a different predetermined time constant, and producing an output signal associated with each signal integrating network. Preferably, the output signal from one of the integrating networks represents the difference between the output of the network and the initial signal, and the remaining output signals represent the difference between the outputs of different ones of the integrating networks. In addition, the output of each of the integrating networks is applied to a root mean square (RMS) network to produce an output from each RMS network which closely approximates the standard deviation for the time constant of the output signal of the associated signal integrating network. The output of each of the RMS networks may then be displayed on a system of light bars or the like, to facilitate comparison of the outputs from the several networks.

As a further aspect of the present invention, the alternating component of the output of an RMS network may be applied to a second RMS network, to produce an output which effectively represents the amplitude variations in the original RMS signal over longer wavelengths of the periodic variations in the monitored parameter. Further, the present invention involves a novel transducer for producing an electrical or other signal which is functionally related to at least one monitored parameter. In one embodiment, the transducer comprises at least two parallel and laterally spaced apart plates, each having an orifice therethrough. The orifices are aligned so as to be adapted to receive the advancing textile strand therethrough, and the size of the orifices in the plates changes to define a vena contracta. If a greater number than two plates is used, then the size of the orifice in the last plates may be larger than the vena contracta and the size expands when viewed in the direction of the advancing textile strand, and so that the advancing strand is compressed upon passing through the vena contracta and then allowed to expand. Further, a force measuring means is mounted to at least a plurality of the plates for continuously measuring the frictional drag on each of the plates, and such that the outputs of the several force measuring means may be compared to reveal various parameters of the advancing strand.

These and other objects and advantages will appear as the description proceeds when taken in connection with the accompanying drawings, in which FIG. 1 is a schematic representation of an apparatus for continuously monitoring the variability of an advancing textile strand in accordance with the present invention;

FIGS. 5-7 are schematic representations of three transducers adapted for use with the present invention;

FIG. 8 is a perspective view of another transducer which is adapted to monitor a number of parameters in a moving yarn strand in accordance with the present invention;

Figure 1:
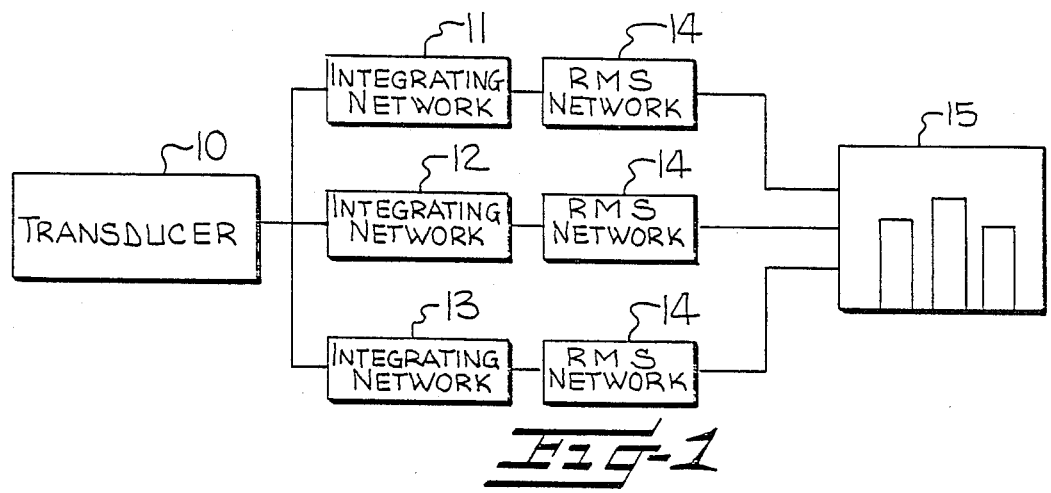

Referring more particularly to the drawings, FIG. 1 schematically illustrates an apparatus which is adapted to continuously monitor the variability of a parameter of an advancing textile strand, in accordance with the present invention. The apparatus includes a transducer 10 which is adapted to continuously monitor at least one selected parameter, such as linear density, and to produce an electric, pneumatic, thermal or other output signal which is functionally related to the monitored parameter. Transducers of various known designs are suitable for this purpose, including the novel transducers as specifically described below with respect to FIGS. 5-12.

Figure 3:
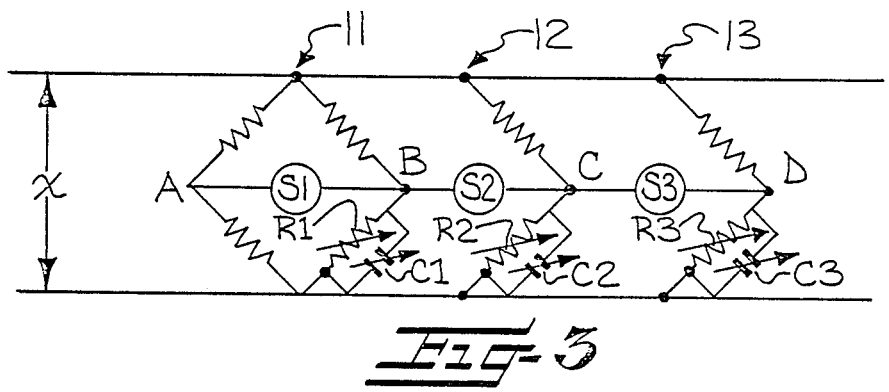
FIG. 3 is a schematic circuit diagram of three resistor-capacitor networks adapted to form the integrating networks illustrated in FIG. 1.

The signal from the transducer 10 typically contains error signals which are superimposed on longer term errors or standing values, and in accordance with the present invention these standing values are separated so as to provide a more accurate representation of the true errors produced in a subject process. For this purpose, the signal from the transducer is applied to each of a plurality of signal integrating or smoothing networks, each having a different time constant. In the embodiment of FIG. 3, an electrical initial signal x is produced by the transducer 10, and the initial signal x is applied to each of a number of resistor-capacitor (RC) networks 11, 12, 13 as illustrated schematically in FIG. 1, which serve to separate out the standing error values within a range of error wavelength bands.

As more specifically illustrated in FIG. 3, each of the RC networks is in the nature of a Wheatstone bridge, with a capacitor shunted across the resistance of one arm. The values of the resistor and capacitor in each such arm are variable, which permits the time constant of the network to be selected. Thus for example, in the RC network 11 having the output labeled S1, the point A receives the transient initial signal x from the transducer, and at point B the initial signal has been smoothed by being integrated over a time period determined by the values of R1, C1. The bridge thus provides an output voltage signal S1 which is the difference between the voltage of the transient initial signal x and the integrated or smoothed voltage, and the voltage of signal S1 is functionally related to the true error content of the initial signal x within a certain error wavelength band. By altering the values of R1 and C1, the transient voltage is compared with an averaged value of a different time period. It will also be understood that the sample length in the continuous process is equal to the time indicated by the value of the resistor and capacitor, times the velocity of the advancing strand. Thus the value of R and C also determines the effective sample length.

Figure 4:
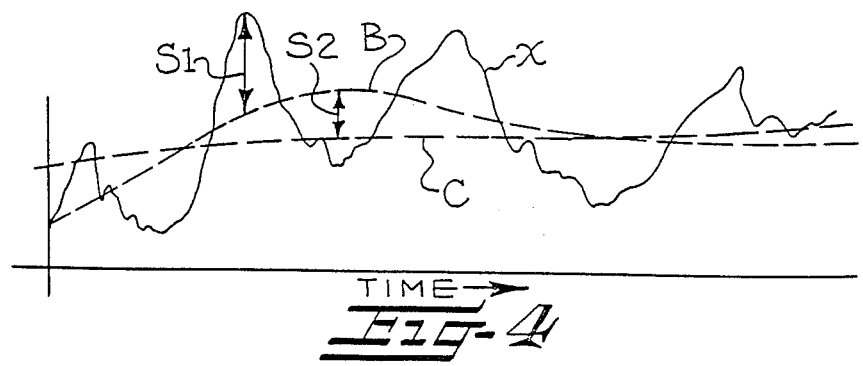
FIG. 4 is a graph illustrating a typical waveform of a monitored parameter of an advancing textile strand.

The second RC network 12 has a time constant represented by R2, C2, which is different from that of the first network, and the output signal S2, which is taken between the points B and C, represents the difference between the integrated signal produced by the network 12 and the integrated signal produced by the network 11. Similarly, the output signal S3, which is taken between the points C and D, represents the difference between the integrated signal produced by the network 13 and the integrated signal produced by the network 12. Thus as illustrated in the graph of FIG. 4, the original initial signal x varies significantly with time, whereas the signal at B represents a running average based upon a relatively short time period determined by R1, C1. The signal at C represents a running average based upon a longer time period established by R2, C2. As will be apparent, the two outputs S1, S2 will be different by reason of the different time periods. The third RC network has a time constant represented by R3, C3, which may be still longer, and which would result in a further smoothing of the running average. Also, the number of these RC networks may exceed the three of the illustrated embodiment, and will be determined by the particular parameters being monitored and strand materials being processed.

As noted above, the three RC networks 11, 12 and 13 illustrated in FIG. 3 include selected values of the resistance and capacitor, so that each network has a different predetermined time constant, and each output signal operates between selected limits of frequency or wavelength. Thus for example, the signal S1 may be set for three inch sample lengths, the signal S2 set at twenty-four inches, the signal S3 set at one hundred ninety-two inches, and so forth to correspond to the draft program used in a particular series of machines.

As a further aspect of the present invention, the output from each of the three networks 11, 12 and 13 is applied to a root mean square (RMS) circuit network 14, which is per se well known in the art, and which produces an output which closely approximates the standard deviation for the time constant of the associated RC network. Further, the output of these RMS networks may be appropriately displayed, such as on a system of light bars 15, and such that the display resembles a spectrogram of the type commonly used in the textile industry. Such a display is adapted to illustrate a form of harmonic analysis of the errors, which is capable of showing transient changes, as the machine to which they are connected processes a variable textile product.

Figure 2:
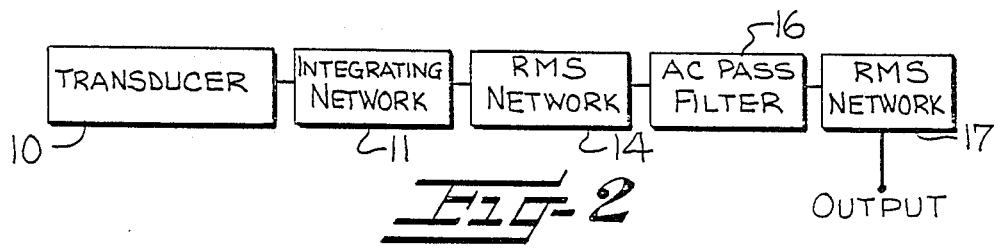
FIG. 2 is a schematic representation of a further aspect of the apparatus, and which includes the use of two serial root mean square networks for processing the error signal.

FIG. 2 schematically illustrates a further embodiment of the present invention, and wherein the output signal from the transducer 10 is applied to an integrating network 11 and an RMS network 14 as described above, and the output from the RMS network is passed through an AC pass filter 16 to remove the standing electrical voltage, and is then applied to a second RMS network 17. In this regard, it will be understood that with a fairly short time constant, the initial RMS network tends to follow the longer wavelengths and indicate the errors relative to that base. Neither the output or standard deviation is a constant, but each has distinct amplitude variations corresponding to the variations in the fiber population. The second RMS circuit network 17 in effect measures the amplitude of these shorter wavelengths as the fiber populations change due to the effects of prior processes. These latter effects become long term changes at the point of measurement and therefore the time constant RC for the second RMS network is made correspondingly longer. The resulting output has been found to be useful in analyzing the periodic variations of the strand, in that the signal permits identification of causes of defects which are not apparent from the original RMS signal.

FIGS. 5-10 illustrate several embodiments of a transducer in accordance with the present invention, and which are adapted to indicate not only the linear density of the advancing strand, but also other important fiber parameters, such as fiber fineness, bulkiness, alignment, and crimp. In the embodiment of FIG. 5, the transducer comprises a tubular sliver trumpet 20 having a port 21 adjacent the vena contracta for sensing the airflow through the trumpet. An electrical pressure transducer 22 of known design is operatively connected to the port 21 for producing an electrical signal which is proportional to the pressure at the port, and thus to the linear density of the advancing strand.

FIG. 6 illustrates a similar transducer which includes a trumpet 20 having a port 21, and an integrating network composed of a storage chamber 24 communicating with the port 21 via a restriction 25. A differential pressure transducer 26 is operatively connected on opposite sides of the restriction 25, for producing an output signal representing the difference between the pressure at the pressure port 21 and the pressure in the storage volume 24 integrated over a time constant determined by the size of the restriction and the capacity of the storage chamber. FIG. 7 illustrates an embodiment where the transducer includes the hot junction 28 of a thermocouple 29 adjacent the vena contracta of the trumpet 20, and an integrating network which includes the known thermal resistance of the thermocouple, a cold junction 30 and the heat sink 31 of a known heat capacity, with the integrating network producing an output electrical signal representing the difference between the temperature of the strand adjacent the vena contracta and the temperature of the heat sink integrated over a time constant determined by the capacity of the heat sink and the thermal resistance of the temperature measuring means. In the embodiments of FIGS. 6 and 7, the integrating networks will be seen to comprise flow paths of fluid or heat, which have resistances to flow and storage devices arranged to provide appropriate time constants, and to provide appropriate comparisons. Thus in these embodiments, the pressure or temperature is the equivalent of the voltage used in the prior embodiments.

Figure 9:
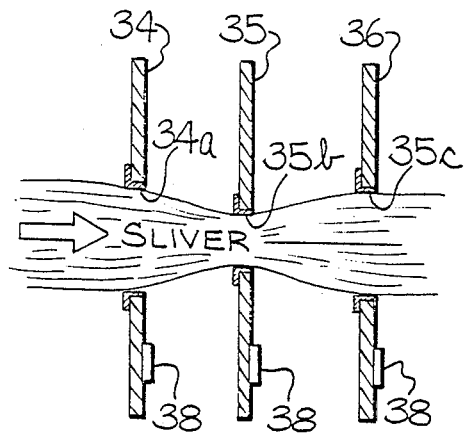
FIG. 9 is a sectional side elevation view of the transducer shown in FIG. 8.

In the embodiment of FIGS. 8 and 9, the transducer 32 comprises three parallel relatively thin plates 34, 35, and 36 which are laterally spaced apart a predetermined distance, with each of the plates having a circular orifice 34a, 35a, and 36a therethrough. The plates are fixedly mounted with respect to each other and with the orifices of the plates being coaxially aligned, and so as to be adapted to receive an advancing textile strand therethrough. Viewed in the direction of the strand advance, the orifice 34a in the initial plate has a relatively large diameter, which is only slightly smaller than the nominal diameter of the strand, the orifice 35a of the middle plate has a substantially smaller diameter, and the orifice 36a of the third plate is approximately equal to that of the initial plate. Thus the middle plate defines a vena contracta, and the advancing strand is compressed upon passing through the vena contracta and then is allowed to expand as it moves through the subsequent plates. In addition, the transducer includes force measuring means, such as a strain gauge 38, mounted to each of the plates for continuously measuring the frictional drag forces on each of the plates. The drag forces are closely related to the lateral compressive force of the strand, and the strain gauges each provide a signal which is related to the mathematical product of the compressive force and the coefficient of friction between the fibers and the orifice plate. Each signal is thus indicative of the linear density.

In addition to linear density, the outputs of the several force measuring means may be compared to reveal various other parameters of the advancing strand. For example, the ratio of the outputs from the gauges of plates 34, 35 is indicative of the transverse modulus of the material, and the ratio of the outputs from the gauges of the plates 34, 36 is indicative of the hysteresis effect, which in turn is indicative of a number of parameters including fiber fineness, bulkiness, alignment, and crimp. By choice of the compared ratios of the outputs of the three plates, these various other parameters may be separated and analyzed.

As an alternative to the strain gauges, air pressure may be applied between the plates and the pressure may be monitored so as to provide an indication of the drag forces. It is also possible to combine these alternatives by using thin orifice plates which act as diaphragms. The air pressure in combination with the drag forces then act on the strain gauges to produce the desired output signal.

Figure 10:
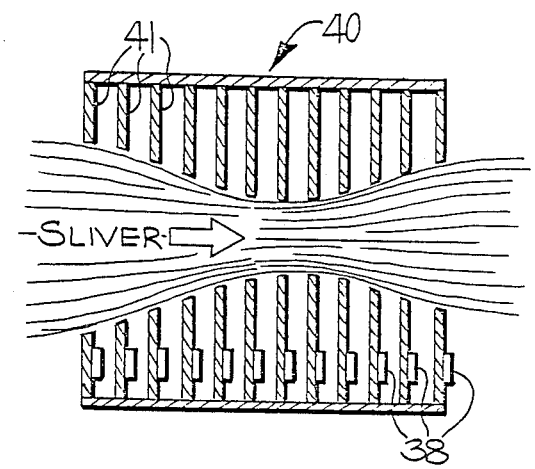
FIGS. 10-12 are sectional views of alternative embodiments of a transducer of the type shown in FIGS. 8 and 9.

FIG. 10 shows a further embodiment of the transducer of the present invention. In this embodiment, the transducer 40 comprises a total of twelve plates 41, with the orifices gradually contracting in the direction of strand advance, and then expanding to define a vena contracta at a centrally located plate. All, or selected ones of the plates may mount a strain gauge 38, which permits more potential comparisons of outputs for a more refined analysis of the various parameters.

Figure 11:
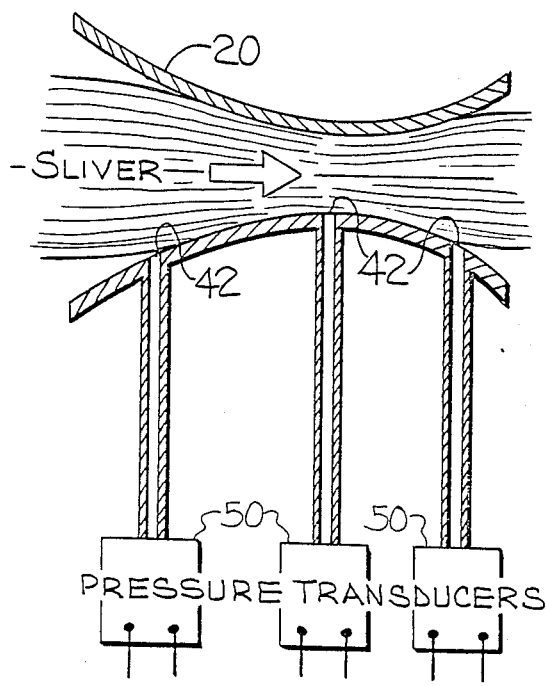
Figure 12:
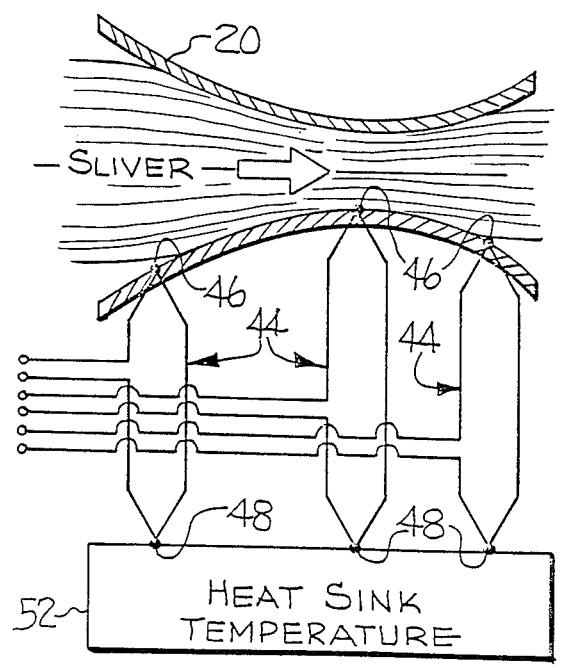

As an alternative embodiment a series of pressure ports 42 may be provided in a trumpet 20 as illustrated in FIG. 11, as a means of defining the forces acting on the advancing sliver or two as it is compressed and relaxed during passage through the trumpet. Each of the ports 42 is connected to a separate pressure transducer 50, in the illustrated embodiment. Further, temperatures may be measured by a number of thermocouples 44 which have their hot junctions 46 spaced at various locations along the length of the sliver trumpet 20, and their cold junctions 48 attached to the heat sink 52 as shown in FIG. 12. As a further alternative, temperature sensitive resistance gauges (not shown) may be used instead of the thermocouples according to already known techniques of measuring temperature differential.

In the drawings and specification there has been set forth preferred embodiments of the invention, and although specific terms are employed, they are used in a generic and descriptive sense only and not for purposes of limitation.

That which is claimed is:

1. A method of continuously monitoring the variability of an advancing textile strand, such as tow, sliver, roving or yarn, to facilitate the quality control analysis of the strand, and including the steps of continuously monitoring at least one selected parameter of the advancing strand and producing a continuous initial signal which is functionally related to said one parameter, applying said initial signal to each of a plurality of signal integrating networks each having a different predetermined time constant, and with each of said signal integrating networks producing a continuous output signal which is representative of a running average of the deviations of said one parameter over a length of the advancing yarn, with such length being determined by the time constant of the integrating network, and whereby the continuous output signals are useful for facilitating the quality control analysis of the strand.

2. The method as defined in claim 1 comprising the further steps of producing a first output signal which represents the difference between the integrated signal produced by a first integrating network and the initial signal, and producing a further output signal which represents the difference between the integrated signal produced by a further network and the integrated signal produced by said first network.

3. The method as defined in claim 1 wherein the step of continuously monitoring each selected parameter includes monitoring the linear density of the advancing strand and wherein said initial signal is an electrical signal.

4. The method as defined in claim 1 comprising the further step of applying each of the output signals of said signal integrating networks to a separate root mean square network for each integrating network to produce a continuous output from each root mean square network which closely approximates a standard deviation of the output signal of the associated signal integrating network, and whereby the continuous outputs of the root mean square networks are useful for facilitating the quality control analysis of the strand.

5. The method as defined in claim 4 comprising the further step of displaying the outputs of each of the root mean square networks to facilitate comparison of the outputs of such networks.

6. A method of continuously monitoring the variability of an advancing textile strand, such as tow, sliver, roving or yarn, to facilitate the quality control analysis of the strand, and including the steps of continuously monitoring at least one selected parameter of the advancing strand and producing a continuous initial signal which is functionally related to the monitored parameter, applying said initial signal to an integrating network having a predetermined time constant, applying the output of the integrating network to a first root mean square network to produce an output which closely approximates a standard deviation for the time constant of said integrating network, and applying the output of said first root mean square network to a second root mean square network to produce an output which effectively represents the long term changes of the periodic variations in the monitored parameter, and whereby the output of said second root mean square network is useful for facilitating the quality control analysis of the strand.

7. The method as defined in claim 6 wherein said initial signal is an electrical signal, and wherein said integrating network comprises a resistor-capacitor network.

8. The method as defined in claim 7 comprising the further step of passing the output of the first mentioned root mean square network through an AC pass filter to substantially remove any standing electrical signal and applying the output of said AC pass filter to said second root mean square network.

9. An apparatus for continuously monitoring the variability of an advancing textile strand, such as tow, sliver, roving or yarn, to facilitate the quality control analysis of the strand, and comprising transducer means for continuously monitoring at least one selected parameter of the advancing strand and producing a continuous initial signal which is functionally related to said one parameter, a plurality of signal integrating networks each having a different predetermined time constant and an output terminal, means operatively interconnecting said initial signal produced by said transducer means to each of said integrating networks, and such that the output terminal of each integrating network produces a continuous output signal which is representative of a running average of the deviations of said one parameter over a length of the running yarn, with such length being determined by the time constant of the integrating network, and whereby the continuous output signals are useful for facilitating the quality control analysis of the strand.

10. The apparatus as defined in claim 9 further comprising first output signal means operatively interconnected between the initial signal and the output terminal of a first one of said integrating networks, and an additional output signal means operatively interconnected between the output terminal of a different one of said integrating networks and said first integrating network.

11. The apparatus as defined in claim 9 further comprising a plurality of root means square networks, and means operatively interconnecting each of said output signal means with one of said root mean square networks.

12. The apparatus as defined in claim 9 wherein said transducer means comprises a tubular trumpet defining a vena contracta and having a sensor adjacent the vena contracta for sensing air pressure, and each of said integrating networks comprises an air storage chamber communicating with said sensor via a duct having a restriction therein, and a differential pressure transducer operatively connected to said duct on opposite sides of said restriction.

13. The apparatus as defined in claim 9 wherein said transducer means comprises a tubular trumpet defining a vena contracta, and each of said integrating networks comprises a heat sink and thermocouple means mounted to said trumpet and to said heat sink.

14. The apparatus as defined in claim 9 wherein said transducer means comprises a tubular trumpet defining a vena contracta and having a sensor adjacent said vena contracta, and a transducer operatively connected to said sensor for producing an electrical signal which is functionally related to the output of said sensor.

15. The apparatus as defined in claim 14 wherein each of said signal integrating networks comprises an electrical resistor-capacitor network.

16. An apparatus for continuously monitoring the variability of an advancing textile strand, such as tow, sliver, roving or yarn, to facilitate the quality control analysis of the strand, and comprising
    transducer means for continuously monitoring at least one selected parameter of the advancing strand and producing a continuous initial signal which is functionally related to said one parameter,
    signal integrating means operatively connected to said transducer means for integrating the initial signal over a predetermined time constant and producing an integrated output signal,
    means operatively connected to the integrated output signal for producing a second output signal representing the root mean square of the integrated output signal, and
    means operatively connected to the second output signal for producing a third output signal representing the root means square of the second output signal.

17. A transducer adapted for monitoring a number of parameters in a moving textile strand and comprising
    strand guide means including a vena contracta having a point of maximum contraction for contracting the moving strand and then permitting the strand to expand, and
    means for measuring at least one parameter at each of a plurality of locations as the moving strand moves through said guide means, with at least one of said locations being adjacent the point of maximum contraction of said vena contracta and where the strand is contracted from its natural size, and with a second of said locations being downstream of such point of maximum contraction and where the strand has expanded from its size at said one location.

18. The transducer as defined in claim 17 wherein said parameter measuring means further comprises a pressure port located at each of said first and second locations and at least one additional pressure port located upstream of said point of maximum contraction.

19. The transducer as defined in claim 17 wherein said parameter measuring means comprises a first thermocouple means having a hot junction located adjacent said vena contracta, a second thermocouple means having a hot junction located on one side of said vena contracta, and a third thermocouple means located on the other side of said vena contracta, and with each of said thermocouple means including a cold junction attached to a heat sink.

20. A transducer adapted for monitoring a number of parameters in a moving textile strand and comprising
    at least two parallel and laterally spaced apart relatively thin plates each having an orifice therethrough, with the orifices being aligned so as to be adapted to receive an advancing textile strand therethrough, and with the size of the orifices being different among the plates, and
    force measuring means mounted to each of said plates for continuously measuring the frictional drag of the advancing textile strand on each of said plates and producing an output which is functionally related to the frictional drag and whereby the outputs of the several force measuring means may be compared to reveal various parameters of the advancing strand.

21. The transducer as defined in claim 20 wherein there are at least three of said plates, with the orifices thereof defining a vena contracta.

22. A transducer adapted for continuously monitoring at least one parameter in a moving textile strand and comprising
    tubular trumpet means for contracting the moving strand and then permitting the strand to expand,
    pressure port means communicating with the tubular trumpet means at a predetermined location for monitoring the air pressure at said predetermined location at which the pressure port means communicates with said trumpet means,
    an air storage chamber communicating with said pressure port means through a duct having a restriction therein, and
    differential pressure transducer means operatively connected to said duct on opposite sides of said restriction for producing an output signal representing the difference between the pressure at said pressure port and the pressure in the storage volume integrated over a time constant determined by the size of said restriction and the capacity of said storage chamber.

23. The transducer as defined in claim 22 wherein said tubular trumpet means defines a vena contracta, and said pressure port means is located adjacent said vena contracta.

24. A transducer adapted for continuously monitoring at least one parameter in a moving textile strand and comprising
    tubular trumpet means for contracting the moving strand and then permitting the strand to expand, said trumpet means defining a vena contracta,
    a heat sink,
    temperature measuring means for measuring the temperature of said strand adjacent said vena contract and of said heat sink for producing an output electrical signal representing the difference between the temperature of said strand adjacent said vena contracta and the temperature of said heat sink integrated over a time constant determined by the capacity of said heat sink and the thermal resistance of said temperature measuring means.

* * * * *